US00PP15163P2

(12) United States Plant Patent
Olesen et al.

(10) Patent No.: US PP15,163 P2
(45) Date of Patent: Sep. 21, 2004

(54) CLEMATIS PLANT NAMED 'EVIPO017'

(50) Latin Name: *Clematis viticella*
Varietal Denomination: EVIpo017

(75) Inventors: Mogens N. Olesen, Fredensborg (DK); Raymond J. Evison, Guernsey (GB)

(73) Assignee: Poulsen Roser A/S, Fredensborg (DK)

( * ) Notice: Subject to any disclaimer, the term of this patent is extended or adjusted under 35 U.S.C. 154(b) by 4 days.

(21) Appl. No.: 10/640,793

(22) Filed: Aug. 13, 2003

(51) Int. Cl.[7] ..... A01H 5/00
(52) U.S. Cl. ..... Plt./228
(58) Field of Search ..... Plt./228

*Primary Examiner*—Kent Bell

(57) ABSTRACT

A new Clematis cultivar which is well suited to propagation in glasshouses. With a tall growth habit, profuse, violet flowers, and continuous summer flowering.

The variety successfully propagates from softwood cuttings and is suitable for cultivation in commercial glasshouses. This new and distinct variety has shown to be uniform and stable in the resulting generations from propagation.

1 Drawing Sheet

Botanical classification: *Clematis viticella.*
Variety name: 'EVIpo017'.
Commercial: Early large flowering cultivar.

SUMMARY OF THE INVENTION/DISCOVERY

The present invention constitutes a new and distinct variety of Clematis which originated from a controlled crossing between Clematis 'Royalty', un-patented and Clematis 'Silver Moon', un-patented. The two parents were crossed and the resulting seed was planted in a controlled environment. The new variety is named 'EVIpo017'.

'Evipo017' may be distinguished from the female seed parent by the following characteristic. 'Royalty' has a much darker purple flower color than 'Evipo017'.

'Evipo017' may be distinguished from the male pollen parent by the following characteristic. While 'Silver Moon' is similar in flower color to the claimed plant, anthers on reproductive parts are different in color. Anthers of 'Evipo017' are more brown colored, while they are yellow in color on 'Silver Moon'.

The objective of the hybridization of this Clematis variety for commercial glasshouse and nursery culture was to create a new and distinct variety with:

1. Light violet flowers.
2. Free flowering, with good repeat flowering.
3. Extremely compact habit.
4. Flowers well as a young plant.
5. Well suited for small containers.

These qualities required improvement in Clematis varieties that were in commercial cultivation and the objectives have been substantially achieved in the new variety, as evidenced by the unique combination of characteristics that are present in 'EVIpo017' which distinguish it from all other varieties of which we are aware.

The seeds from the hybridization were germinated and evaluations were conducted of the resulting Clematis plants in a controlled environment. 'EVIpo017' was selected by Raymond J. Evison and Mogens N. Olesen in their Clematis development program in Domarie Vineries Les Sauvagees, St. Sampsons, Guernsey, Channel Islands, United Kingdom in April of 1998.

Asexual reproduction of 'EVIpo017' by cuttings was first done by Raymond J. Evison and Mogens N. Olesen in Domarie Vineries Les Sauvagees, St. Sampsons, Guernsey, Channel Islands, United Kingdom in May 1998. This initial and subsequent propagations have demonstrated that the characteristics of 'EVIpo017' are true to type and are transmitted from one generation to the next.

BRIEF DESCRIPTION OF THE DRAWING

The accompanying color illustration show as true as is reasonably possible to obtain in color photographs of this type:

FIG. 1.1 Young stem showing attachment of juvenile leaves with pedicel and closed flower bud.

FIG. 1.2 Mature foliage with petiole, petioloule, and leaflets.

FIG. 1.3 Flowering stem with closed flower buds and open flower attached. Open flower and closed flower bud, detached.

FIG. 1.4 Open flower, upper surface.

FIG. 1.5 Open flower, lower surface.

DETAILED DESCRIPTION OF THE VARIETY

The following is a detailed description of 'EVIpo017', as observed in its growth throughout the flowering period in glasshouses at Domarie Vineries Les Sauvagees, St. Sampsons, Guernsey, Channel Islands, United Kingdom. The observed plants were grown in 2 liter pots in an unheated greenhouse for 2 years. Certain phenotypical characteristics of the variety may vary under different environmental, cultural, agronomic, seasonal, and climatic conditions. Color references are made using The Royal Horticultural Society (London, England) Colour Chart, 1995.

For a comparison, the nearest existing Clematis variety is 'EVIrin', a patented variety described and illustrated in U.S. Plant Pat. No. 12,838 and issued on Aug. 13, 2002. Chart 1 details several physical characteristics of 'Evipo017' and 'Evirin'.

CHART 1

| | 'EVIpo017' | 'EVIrin' |
|---|---|---|
| Growth | Compact: 1 to 1.5 Meters | Greater than 2.0 Meters |
| Flower diameter | 100–130 mm | 120–160 mm |
| Tepal arrangement | All tepals overlap | tepals join or overlap only slightly |
| Tepal shape | Broad ellipse | Narrow elliptic |

Pollen parent: 'Silver Moon'.
Seed parent: 'Royalty'.

FLOWER AND FLOWER BUD

Blooming habit: Recurrent.
Flower bud:
*Size.*—20 to 30 mm in length. Bud diameter is 15 to 25 mm.
*Bud form.*—Ovoid.
*Bud color.*—Green Group 138C at ¼ open.
*Peduncle.*—Surface: Smooth. Length: 60 to 90 mm average. Color: Green Group 137C. Strength: Strong, erect.
*Borne.*—In compound cymes. Early season flowers occasionally borne singly.
Flower bloom:
*Size.*—100 to 130 mm in diameter. Typically, flowers are 30 mm in depth.
*Form.*—Upon opening, flat to concave, with tepals normally straight.
*Color.*—Upon opening, the upper surface of the tepals is Violet Group 85A. The reverse side is Violet Group 85C with a bisecting line of Green Group 137D extending the length of the tepal. After opening, the upper surface is Violet Group 85A with intonations of Violet Group 85D at the basal zone. The reverse side is Violet Group 85C with a bisecting line of Green Group 137D extending the length of the tepal.
*Variations.*—None observed.
*Fragrance.*—Light.
*Duration.*—Flowers have a duration on the plant from 5 to 10 days.
Tepals:
*Tepal count.*—Double. Average number of tepals is 8. Average range is 6 to 8.
*Shape.*—Individual tepal shape is broadly elliptic. Base and apex are rounded.
*Size.*—Length is 50 to 65 mm. Width is 40 to 50 mm.
*Cross section.*—Flat.
*Margin.*—Entire with a point in the center. Margins have weak undulations.
*Tepal apex.*—Rounded.
*Recurvature of tip.*—None.
*Persistence.*—Tepals drop cleanly from plant.
*Arrangement.*—Tepals are arranged regularly.
Reproductive organs:
*Pollen.*—Quantity: Average. Color: Yellow Group 2D.
*Anthers.*—Size: 7 to 10 mm. Color: Yellow Group 2D with intonations of Red Purple Group. 72A expressed as a longitudinal segment. Arrangement: Regular.
*Filaments.*—Color: White Group 155D. Size: 10 to 12 mm.
*Stigmas.*—Color: Yellow Group 2D. Location: As the inflorescence matures, stigmas protrude between the anthers.
*Styles.*—Color: Yellow Group 2D.
*Pistils.*—Quantity: 85 to 110.

PLANT

Plant form: Climbing and spreading.
Plant growth: Very compact and slow growing.
Spread: 0.5 to 1 meter.
Height: Seasonal growth 1 to 1.5 meters.
Hardiness: Trials to date show the variety is cold tolerant to USDA Hardiness Zones 4–9.
Stems:
*Color.*—Older wood: Greyed Red Group 178B. After several seasons, color changes to Greyed Orange Group 165C.
*Internodes.*—Cylindrical. Length: 80 to 150 mm.
*Dimensions.*—Diameter is 2 mm. Length of stems from base of plant to flower is typically 0.8 to 1 meter.
*Petioles.*—Size: Average length: 60 to 90 mm. Petioloule Size: 15 to 50 mm. Color: RHS 59 A. Clasping: Winding leaf petiole.
*Bark.*—Young wood: Smooth. Older wood: Smooth.
Plant foliage: Deciduous. 3 Ovate Leaves arranged in pinnate form.
*Terminal leaflet size.*—50 to 70 mm (l)×40 to 60 mm (w).
*Compound leaf size.*—180 mm (l)×100 mm (w).
*Abundance.*—Average.
*Color.*—Mature Foliage is Green Group 137A at the upper surface. Green Group 137C on the reverse side. Juvenile Foliage is Green Group Green Group 137C at the upper surface. Green Group 137C on the reverse side.
Plant leaves and leaflets:
*Stipules.*—Absent.
*Petiole.*—Length: 60 to 90 mm. Underneath: Smooth.
*Leaf edge.*—Terminal leaflet margin is entire.
*Shape.*—Base of leaflet: Rounded. Apex of leaflet: Acute.
*Texture.*—Upper side: Glabrous. Lower side: Ribbed.
*Thickness.*—Medium.
*Glossiness.*—Matte Finish.
Disease resistance: Subject to any disease that normally attacks the species.

We claim:

1. A new and distinct variety of Clematis plant named 'Evipo017', as illustrated and described herein as a distinct and novel clematis variety due to its abundant violet flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

EVIpo017
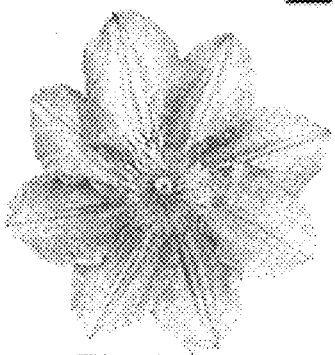
Fig. 1.4
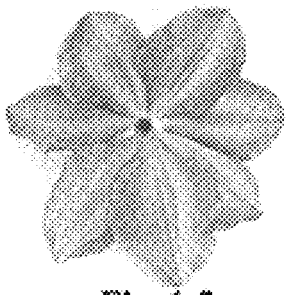
Fig. 1.5
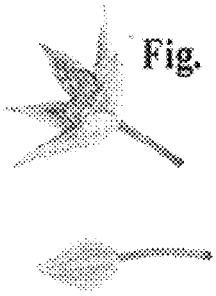
Fig. 1.3
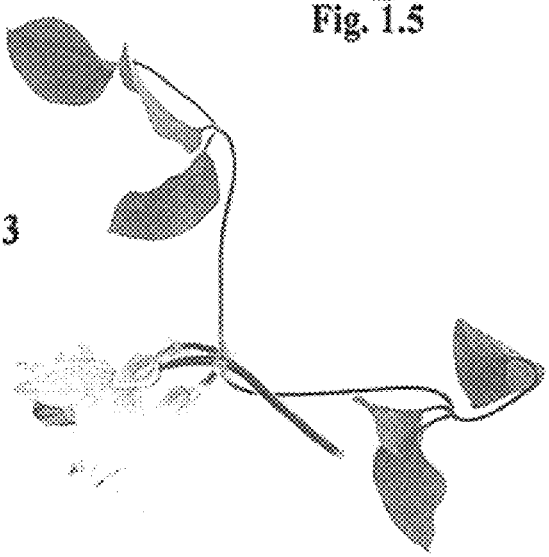
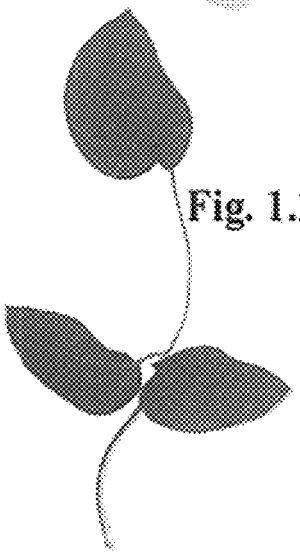
Fig. 1.2
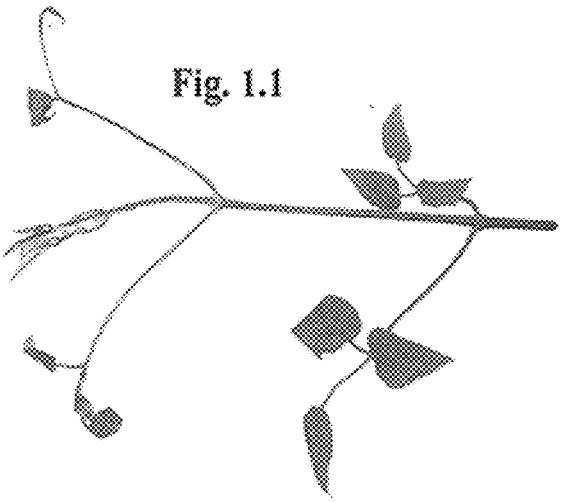
Fig. 1.1